United States Patent
Wiley

(10) Patent No.: US 11,944,572 B2
(45) Date of Patent: *Apr. 2, 2024

(54) PHACOEMULSIFICATION TIP

(71) Applicant: William F. Wiley, Chagrin Falls, OH (US)

(72) Inventor: William F. Wiley, Chagrin Falls, OH (US)

(*) Notice: Subject to any disclaimer, the term of this patent is extended or adjusted under 35 U.S.C. 154(b) by 56 days.

This patent is subject to a terminal disclaimer.

(21) Appl. No.: 17/328,668

(22) Filed: May 24, 2021

(65) Prior Publication Data

US 2021/0346200 A1 Nov. 11, 2021

Related U.S. Application Data

(63) Continuation of application No. 15/164,427, filed on May 25, 2016, now Pat. No. 11,033,428.

(60) Provisional application No. 62/166,450, filed on May 26, 2015.

(51) Int. Cl.
*A61F 9/007* (2006.01)
*A61M 1/00* (2006.01)
*A61M 37/00* (2006.01)

(52) U.S. Cl.
CPC ...... *A61F 9/00745* (2013.01); *A61F 9/00709* (2013.01); *A61F 9/00736* (2013.01); *A61F 9/00754* (2013.01); *A61M 1/84* (2021.05); *A61M 37/0092* (2013.01); *A61M 2210/0612* (2013.01)

(58) Field of Classification Search
CPC .............. A61F 9/00709; A61F 9/00736; A61F 9/00745; A61F 9/00754; A61F 9/00763; A61M 1/84; A61M 1/87; A61M 2025/006; A61M 2025/0073; A61M 2206/20; A61M 2210/0612; A61M 37/0092; A61M 1/842

See application file for complete search history.

(56) References Cited

U.S. PATENT DOCUMENTS

| | | | |
|---|---|---|---|
| 5,980,529 A | 11/1999 | Strukel | |
| 6,159,175 A * | 12/2000 | Strukel | A61M 1/743 604/35 |
| 6,283,974 B1 | 9/2001 | Alexander | |

(Continued)

OTHER PUBLICATIONS

International Preliminary Report on Patentability and Written Opinion of the International Searching Authority for International Application No. PCT/US2016/034224, dated Nov. 28, 2017.

(Continued)

*Primary Examiner* — Shefali D Patel
(74) *Attorney, Agent, or Firm* — DeWitt LLP

(57) ABSTRACT

A phacoemulsification tip, including an aspiration tube presenting a cutting tip at a distal end. The aspiration tube has a tube wall presenting an internal face and an external face. The internal face supports at least one internally extending internal ridge. The at least one internal ridge presents an internal distal face, an internal proximal face and an internal apex. The internal distal face meets the internal face at an acute angle measured internally. The at least one internal ridge is structured to engage lens fragments separated from a crystalline lens to enhance proximal movement of the lens fragments and to inhibit distal movement of the lens fragments through the aspiration tube.

21 Claims, 7 Drawing Sheets

(56) References Cited

U.S. PATENT DOCUMENTS

| | | | |
|---|---|---|---|
| 6,984,220 B2 * | 1/2006 | Wuchinich | A61B 17/320068 |
| | | | 606/169 |
| 7,601,136 B2 | 10/2009 | Akahoshi | |
| 8,133,277 B2 | 3/2012 | Scholz | |
| 8,287,484 B2 * | 10/2012 | Rockley | A61F 9/00745 |
| | | | 606/107 |
| 8,771,301 B2 | 7/2014 | Boukhny et al. | |
| 2004/0199171 A1 * | 10/2004 | Akahoshi | A61F 9/00745 |
| | | | 606/166 |

OTHER PUBLICATIONS

International Search Report and Written Opinion for International Application No. PCT/US2016/034224, dated Sep. 12, 2016.
Application and File History for U.S. Appl. No. 15/164,427, filed May 25, 2016. Inventor: William F. Wiley.

* cited by examiner

PHACOEMULSIFICATION TIP

CROSS-REFERENCE TO RELATED APPLICATION

This application is a continuation of application Ser. No. 15/164,427, filed May 25, 2016, entitled "Phacoemulsification Tip," which claims the benefit of U.S. Provisional Application No. 62/166,450, filed May 26, 2015, entitled "Phacoemulsification Tip," each of which is hereby fully incorporated herein by reference.

BACKGROUND

Phacoemulsification is a known ocular surgical procedure for removing cataracts that is commonly practiced.

A cataract occurs when the natural crystalline lens of the eye becomes cloudy or opacified. This results when there is an accumulation of proteins in the natural crystalline lens, which become clumped together over time, thereby causing light scattering. As such, the interference with the passage of light through the natural crystalline lens causes images to become cloudy and distorted and can eventually lead to vision loss sufficient to require treatment. Therefore, several surgical procedures, including phacoemulsification, have been developed to treat cataracts and to prevent vision loss or to restore lost vision. The procedures facilitate removal of the clouded crystalline lens and, nearly always, the placement of an intraocular lens implant to replace the focusing power of the removed natural lens.

The phacoemulsification procedure generally involves the use of an ultrasonic hand-held device including a needle like tip, which is inserted into the eye to facilitate removal of the affected lens. During a typical procedure, a small incision is made near the outer edge of the cornea to allow for the insertion of the surgical device into the eye. Once inserted, the needle tip vibrates ultrasonically to fragment the lens for aspiration and removal. After the natural lens is substantially completely removed, a prescription intraocular lens implant is implanted into the lens capsule to replace the removed natural lens and its focusing power.

In addition to the needle tip, the phacoemulsification device further includes a suction channel and an irrigation sleeve surrounding the needle tip. The suction channel is housed within a hollow cross sectional area of the needle tip and is used to aspirate the fragmented pieces of the lens from the eye during the procedure. The irrigation channel is used to introduce an aqueous solution, usually a balanced salt solution, into the eye to aid in flushing and aspirating the fragmented lens. Although the procedure has proven to be highly effective, issues can arise in the context of severely diseased opacified lens. For example, as the development of a cataract progresses, the lens and, in particular, the lens nucleus becomes denser and harder, thus making removal more difficult. To address such concerns various techniques have been introduced that provide increased efficiency.

In one conventional approach, phacoemulsification devices including geometrical structures arranged along an edge or outer surface of the cutting tip are used in an effort to increase the cutting efficiency of the device during torsional or longitudinal movement. Some other conventional approaches include the use of ring shoulders including energy enhancement cavities that provide increased ultrasonic intensity during lens removal. Additionally, other devices use effect elements arranged across or within a cross sectional area of the cutting tip to reduce clogging of the device.

Drawbacks to such conventional approaches include the inability to effectively fragment lenses that have become excessively hardened or which provide increased emulsification capabilities along a linear path. Other drawbacks include that current phacoemulsification devices may require excessive energy to remove the material of the lens nucleus and that the energy must be applied to nearly pulverize the lens material to accomplish removal.

Excess application of ultrasonic energy in the eye can have negative effects, including damage to the corneal endothelium which can lead to compromise of corneal health. Other ocular structures may be harmed as well by excess ultrasonic energy application.

Thus, there remains a need for an improved phacoemulsification device and improved phacoemulsification procedures.

SUMMARY OF THE INVENTION

Embodiments of the invention solve many of the above discussed problems and include a phacoemulsification tip having grooves or structures at least on the inside of the tip to encourage and facilitate the passage of lens fragments that are separated from the lens during phacoemulsification to be aspirated into the tip and aspirated out of the eye. The grooves or structures may also facilitate or encourage aspiration of fluid from the eye and fluid flow into and through the suction channel. According to another example embodiment of the invention, grooves are structured on the outside of the tip as well to minimize the tendency for the lens being phacoemulsified from moving away from the tip due to ultrasonic vibration and to encourage maintenance of contact between the tip and the lens material.

It has been observed during phaco-emulsification surgery that when the phacoemulsification needle or tip is placed in proximity of or in contact with portions of the crystalline lens inside the eye there is a tendency for the lens or lens fragments to move away from the phacoemulsification tip due to the ultrasonic vibration of the tip. On occasion, fragments of the lens are aspirated into the hollow phaco tip but then to pass out of the hollow phaco tip again thereafter requiring that they be aspirated a second time or further times before they are actually removed from the eye and/or that the fragments sufficiently pulverized prior to aspiration and removal.

As is known to those skilled in the art, it is preferable to minimize the amount of ultrasonic energy introduced into the eye during phacoemulsification to protect the well being of the cells of the corneal endothelium as well as other structures of the eye. Additional time spent in phacoemulsification leads to additional application of ultrasonic energy to the eye and a greater potential that the cells of the corneal endothelium or other structures will be damaged by excess ultrasonic energy. Accordingly, any improvement made to the phacoemulsification tip to expedite the removal of material by aspiration from the eye is expected to minimize the time and energy application required for phacoemulsification and, thus, to reduce the risk of occurrence of endothelial damage that might occur because of excess application of ultrasonic energy during the procedure. It is expected that embodiments of the invention will reduce the amount of energy required to fragment and remove the lens material and to permit removal of material of the lens nucleus with less application of ultrasonic energy to the eye.

According to an example embodiment of the invention, a phacoemulsification tip includes at least one groove or ridge within the aspiration tube of the phacoemulsification tip. In an example embodiment the grooves or ridges are circumferentially oriented. The grooves or ridges maybe parallel or otherwise oriented. According to another embodiment of the invention, at least several grooves or ridges are formed inside of the phacoemulsification aspiration tip. According to another embodiment of the invention, the structure inside of the tip has a shallow distal slope and a steeper proximal slope. The internal structures may be annular in shape and cover the entire interior circumference of the phacoemulsification aspiration tip or may be interrupted in such a way that there are several independent structures located about the circumference. In general, the structures may be sloped in such a way as to be directed distally relative to the tip thereby tending to direct aspirated material and fluid in the direction of aspiration and tending to prevent aspirated material from traveling backwards away from the direction of aspiration. Furthermore, the structures or grooves may be oriented in a spiral or helical pattern to facilitate removal of aspirated material when the phacoemulsification tip is being energized to move in a longitudinal, torsional or elliptical fashion which is expected to facilitate more unidirectional movement of lens material in the aspiration direction. The internal structures or grooves may have a structure similar to that of the rifling of the interior of a rifle barrel or may include an auger or screw like structure.

According to another example embodiment of the invention, grooves or outwardly extending structures are located on the exterior of the phacoemulsification tip either alone or in combination with the structures on the interior phacoemulsification tip. The exterior structures, according to another example embodiment, have a shallower distal slope and a steeper proximal slope. It has been observed that there is a tendency for the crystalline lens to be pushed away from the phacoemulsification tip by the movement and the ultrasonic action of the vibrating tip. The exterior structures are expected to have a tendency to engage the crystalline lens and thereby tend to draw the crystalline lens closer to the phacoemulsification tip thereby at least reducing the tendency of the crystalline lens to move away from the tip during the procedure. The exterior structures are also expected to facilitate distal fluid flow alongside the phacoemulsification tip.

The exterior wall structures may include a single annular ridge extending around the exterior of the phacoemulsification tip or multiple annular ridges extending around the exterior of the phacoemulsification tip. Further, the exterior structures may be annular and continuous about the tip or it may be interrupted about the circumference of the exterior of the phacoemulsification tip.

The exterior structures may also have a spiral or auger like structure. The exterior structures may also be somewhat like a rifled barrel but on the outside rather than on the inside of the tubular structure.

According to another embodiment of the invention, the invention includes a method of phacoemulsification utilizing a tip as described in the embodiments above.

An example method includes inserting a phacoemulsification tip into the eye through an incision, contacting a crystalline lens with the tip, encouraging aspiration of lens fragments through the tip by the presence of distally directed structures within an aspiration lumen of the tip or engaging the lens with distally directed structures located on an exterior of the phacoemulsification tip.

According to another embodiment of the invention, the invention includes a method of removing a lens from an eye by phacoemulsification including applying a phacoemulsification tip of the type described herein in a phacoemulsification procedure.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
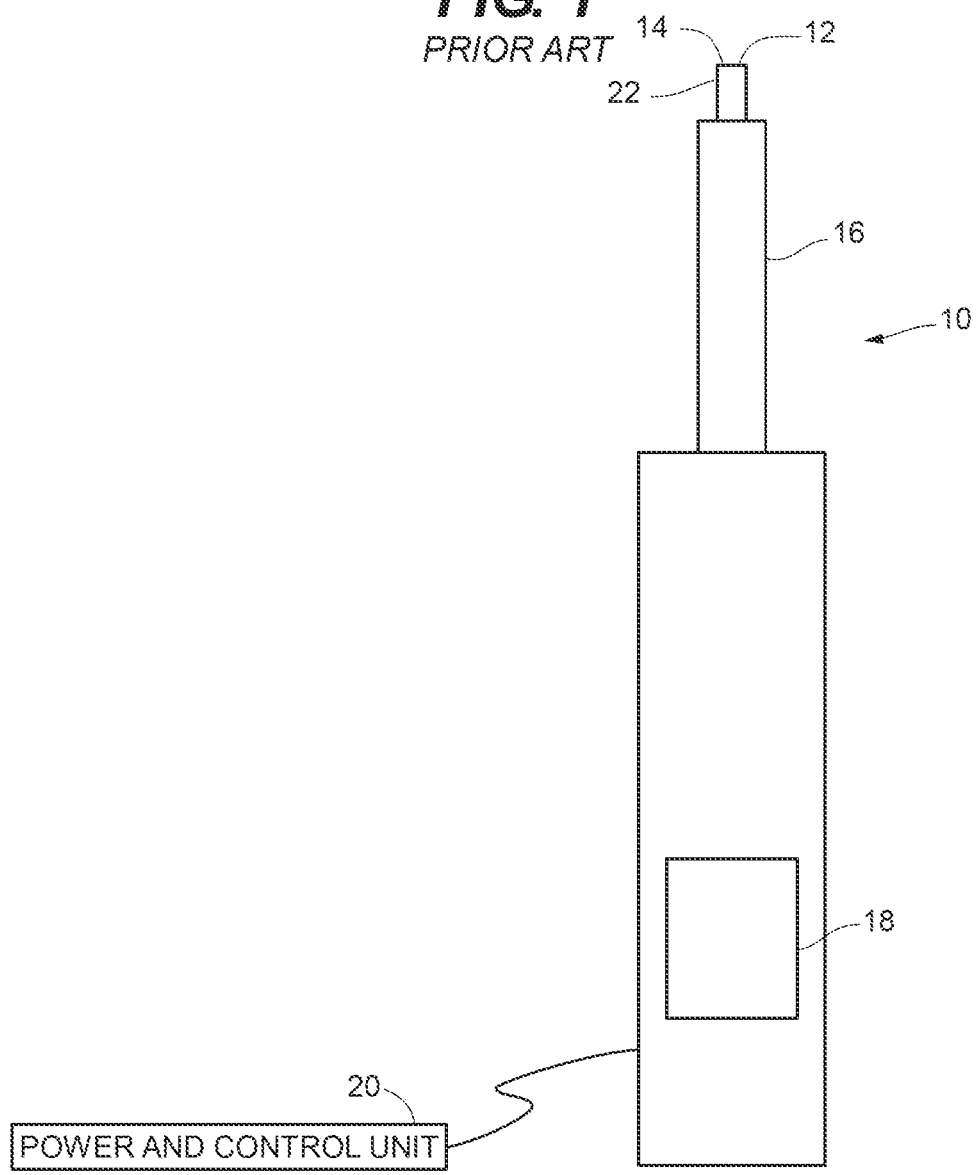
FIG. 1 is a schematic depiction of a phacoemulsification hand piece according to the prior art.
Figure 2:
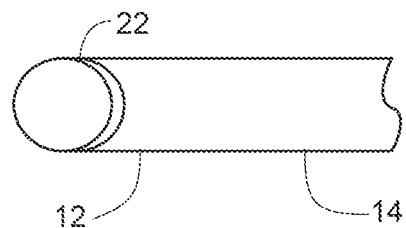
FIG. 2 is perspective view of a conventional phacoemulsification tip according to the prior art.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Referring to FIG. 1, ultrasonic phacoemulsification handpiece 10 according to the prior art generally includes cutting tip 12, aspiration tube 14, irrigation passage 16, ultrasonic resonator 18, and power and control unit 20.

Generally cutting tip 12 is located at a distal end of aspiration tube 14 extending outwardly therefrom. Aspiration tube 14 is generally coupled to a source of suction (not shown) located in power and control unit 20. Irrigation passage 16 generally annularly surrounds aspiration tube 14 and cutting tip 12 extends outwardly beyond irrigation passage 16. Irrigation passage 16 is coupled to a source of irrigation fluid, for example a balanced salt solution, to replace fluid removed from the eye by aspiration.

Ultrasonic resonator 18 is located inside handpiece 10 and serves to ultrasonically vibrate cutting tip 12 when energy is applied to ultrasonic resonator 18. Ultrasonic resonator 18 may vibrate cutting tip 12 torsionally or longitudinally or a combination of the two. A combination of longitudinal and torsional vibration may be referred to as elliptical vibration.

Power and control unit 20 supplies energy to ultrasonic resonator 12, supplies irrigation fluid to irrigation passage 16 and supplies vacuum to aspiration tube 14 to facilitate the aspiration of material separated by cutting tip via aspiration tube 14.

Generally, cutting tip 12 is a substantially cylindrical structure formed as a hollow tube having a lumen therein. Generally distal end 22 of cutting tip 12, according to the prior art, may have a somewhat sharper edge or some structure to facilitate cutting and removal of material.

Figure 3:
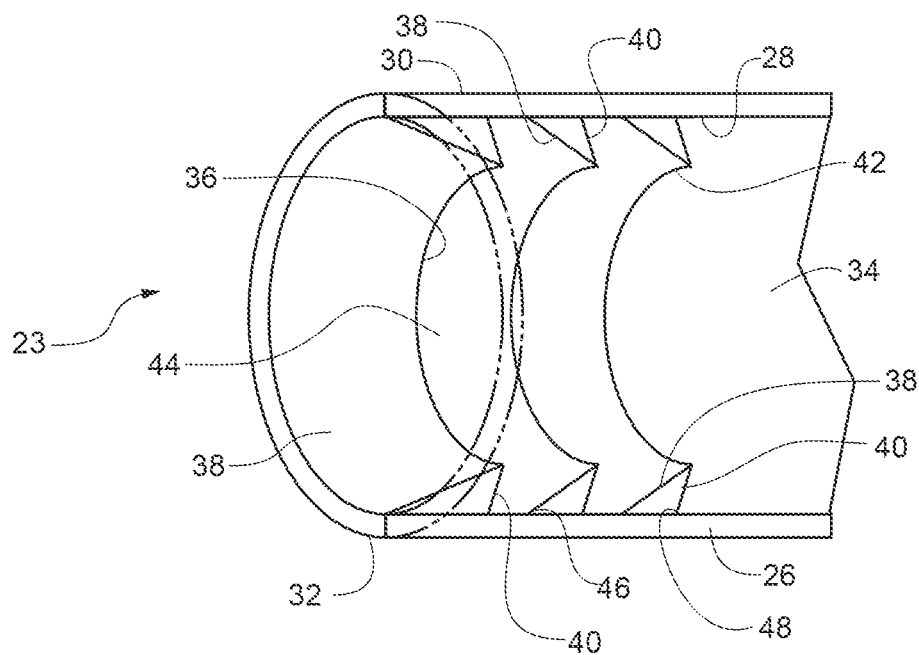
FIG. 3 is a perspective cut-away view of phacoemulsification tip according to an example embodiment of the invention.

Referring to FIG. 3, internal feature tip 23, according to an example embodiment of the invention, is depicted. Internal feature tip 23 generally includes aspiration tube 24 having tube wall 26. Tube wall 26 presents internal face 28, external face 30 and distal end 32. Tube wall 26 surrounds and defines lumen 34.

According to the depicted example embodiment, internal face 28 supports at least one internal ridge 36. Internal ridge 36 generally includes distal face 38, proximal face 40 and apex 42. Internal ridge 36 is generally integrally formed with tube wall 26 that may also be separately formed and secured to tube wall 26 by welding, brazing or adhesives. If more than one internal ridge 36 is present, groove 44 lies between adjacent internal ridges 36.

Distal face 38 is located closer to distal end 32 than proximal face 40. Distal face 38 generally meets internal face 28 at an acute angle as measured from within the structure of internal ridge 36. According to an example embodiment of the invention, proximal face 40 generally meets internal face 28 at an obtuse angle or a right angle as measured from within internal ridge 36.

Figure 5:
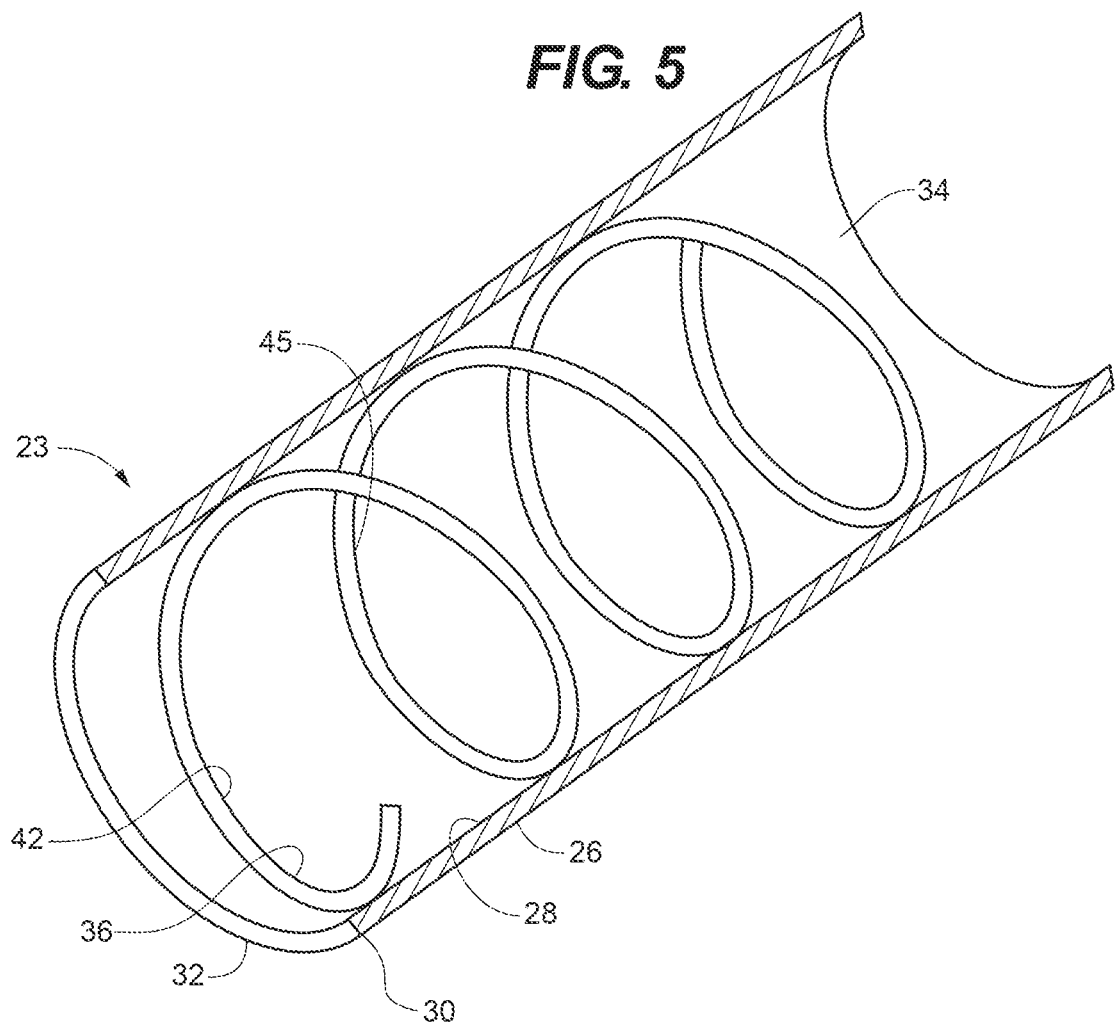
FIG. 5 is a perspective cut-away view of a phacoemulsification tip including internal helical ridges according to an example embodiment of the invention.

Distal face 38 may be flat, concave or convex in cross-section. Proximal face 38 may also be flat, concave or convex in cross-section. Apex 42 is expected to be a generally sharp corner though a rounded corner is also contemplated as part of the invention. While internal ridge 36 is depicted as being annular and continuous about the circumference of internal face 28 in FIG. 3, internal ridge 36 may also be interrupted or may be made in a spiral fashion as helical internal ridge 45 depicted in FIG. 5.

Figure 4:
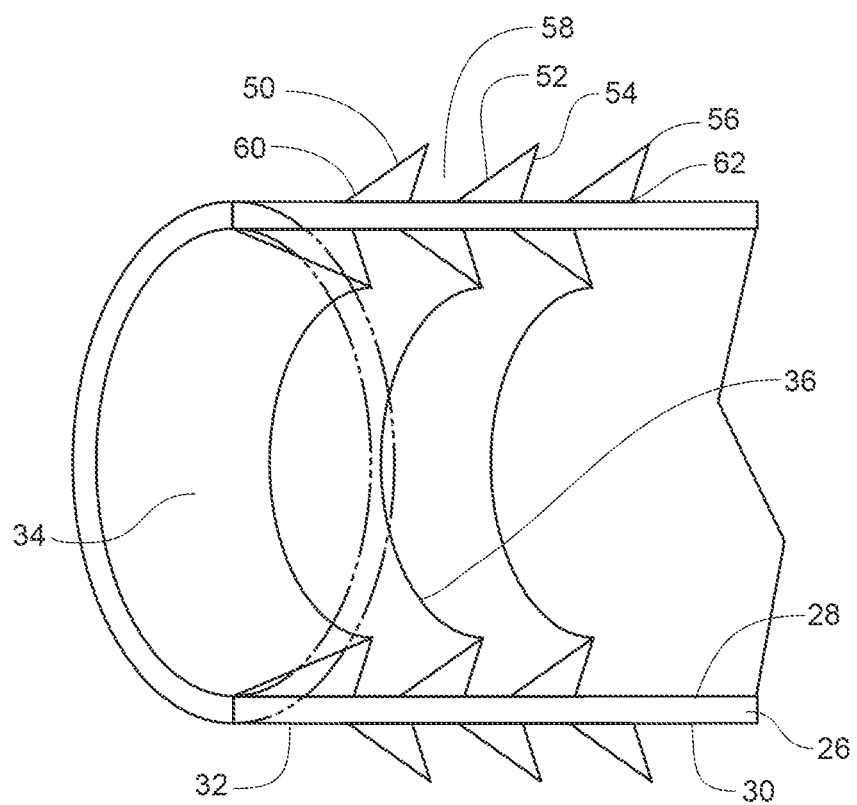
FIG. 4 is a perspective cut-away view of a phacoemulsification tip according to an example embodiment of the invention.
Figure 6:
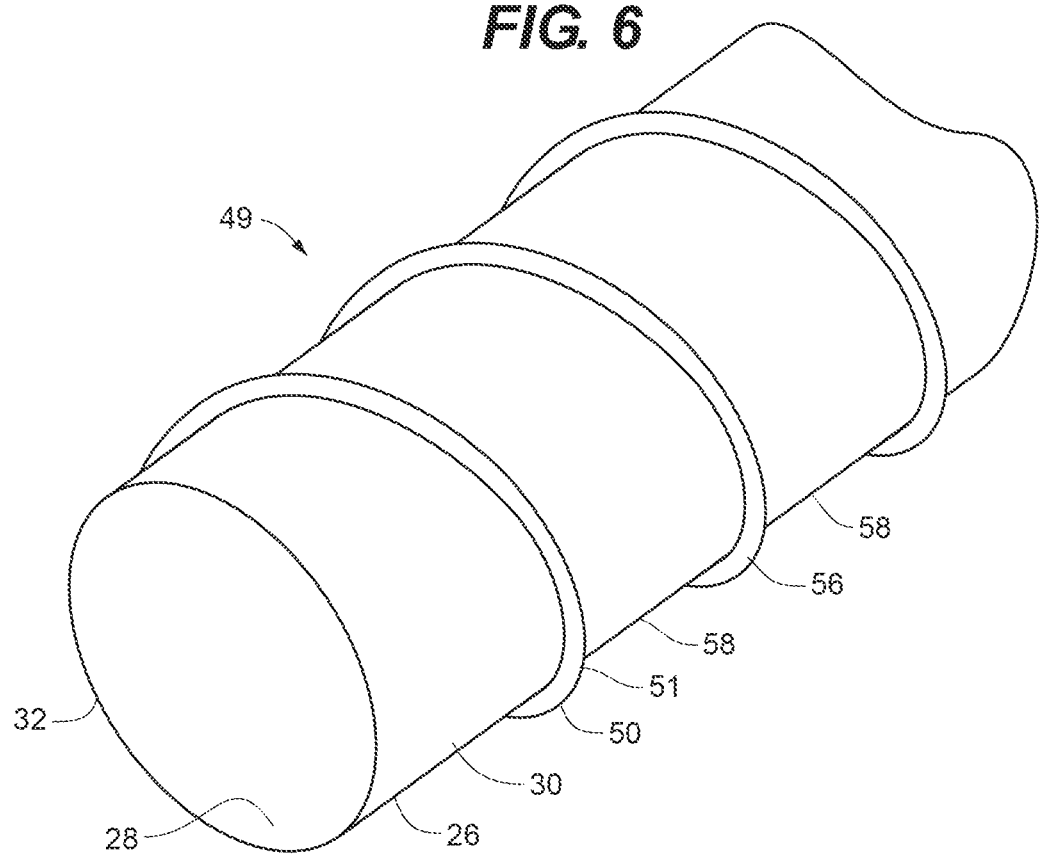
FIG. 6 is a perspective view of a phacoemulsification tip including external helical ridges according to an example embodiment of the invention.

Referring now to FIG. 4, another example embodiment of the invention, presenting external feature tip 49 is depicted. In the depicted embodiment, external face 30 of tube wall 26 supports at least one external ridge 50. External ridge 50 may be annularly oriented and continuous or, may be annular and interrupted. External ridge 50 may include helical external ridge 51 as depicted in FIG. 6, the spiral or helical structure may also be interrupted or continuous.

External ridge 50 generally presents external distal face 52, external proximal face 54 and external apex 56. Similar to internal ridge 36, external distal face 52 generally meets external face 30 at an acute angle 60. According to an example embodiment, external proximal face 54 generally intersects external face 30 at a right or obtuse angle 62. External distal face 52 may be flat in cross-section, concave or convex in cross-section. External proximal face 54 may also be flat, concave or convex in cross-section. If more than one external ridge 50 is present, external groove 64 is defined by adjacent external ridges 50. External apex 56 is expected to be generally sharp in cross-section though external apex 56 may be rounded according to example embodiments of the invention.

Figure 7:
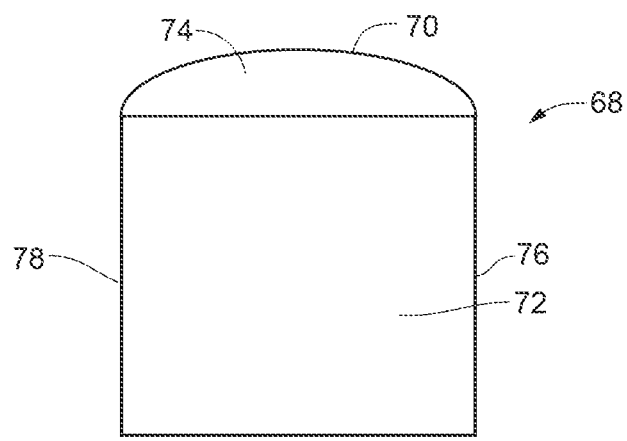
FIG. 7 is a perspective view of a pumping structure according to another example embodiment.

Referring to FIG. 7, another embodiment of internal feature tip 23 is depicted. Aspiration tube 14 includes pumping structures 68 one of which is depicted. Pumping structures 68 extend from internal face 28 inwardly into lumen 34. Pumping structures 68 present curved face 70, flat face 72, inner edge 74, first edge 76 and second edge 78. When aspiration tube 14 is vibrated torsionally pumping structures are expected to create lift much like an airfoil. This creates a vacuum or pumping action to urge fluid unidirectionally down lumen 34. This at least assists the aspiration of fluid and lens fragments out of the eye during phacoemulsification.

Figure 8:
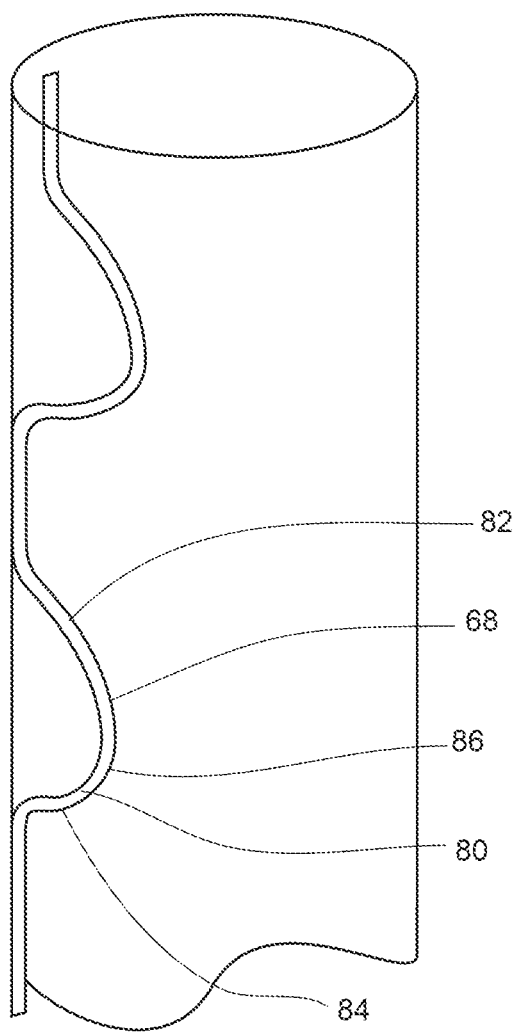
FIG. 8 is a partially cut away view of an aspiration tube including a further pumping structure according to another example embodiment.

Referring to FIG. 8, another embodiment of internal feature tip 23 is depicted. Aspiration tube 14 includes pumping structures 68 depicted. In the depicted embodiment, pumping structure 68 presents curved shape 80 having distal slope 82, proximal slope 84 and crest 86. In the depicted embodiment distal slope 82 is a shallower slope while proximal slope 84 is a steeper slope compared to distal slope 82. Crest 86, as depicted, is gently curved but can be sharper. It is expected that when aspiration tube 14 is ultrasonically vibrated longitudinally, torsionally or elliptically curved shape 80 of pumping structure 68 least assists the aspiration of fluid and lens fragments out of the eye during phacoemulsification.

In operation, an ultrasonic phacoemulsification handpiece 10 equipped with internal feature tip 23 is applied through an incision in the eye and through a capsulorhexis opening made in the lens capsule of an eye to the crystalline lens therein. Typically the crystalline lens will be affected by a cataract. It is expected that in operation, when distal end 32 of internal feature tip 23 is placed in contact with the lens, internal ridges 36 will increase the likelihood that fragments of the crystalline lens drawn into lumen 34 will be aspirated through aspiration tip 24 more efficiently than in a conventional phacoemulsification cutting tip 12. Apex 42 of internal ridge 36 or internal ridges 36 are expected to tend to prevent the outward movement of lens fragments from aspiration tube 24. It is further expected that internal ridges 36 and external ridges 50 will facilitate or assist in fluid flow thus assisting in the pumping of aspiration tip 24 as well as facilitating fluid flow past the outside of aspiration tip 24 in a proximal direction.

Ultrasonic resonator 18 may vibrate cutting tip 12 longitudinally or torsionally.

Further, in operation of internal feature tip 23 also having an external ridge 50 or external ridges 50, it is expected that contact between external ridges 50 with the material of the crystalline lens being phacoemulsified will encourage the structural material of the crystalline lens to remain in contact with distal end 32 of internal feature tip 23 also having external ridges 50. In particular, external apex 56 is expected to engage material of the crystalline lens. It is expected that enhanced friction and mechanical engagement between the external ridges 50 and the lens material will reduce the tendency of the lens to move away from external feature tip 49.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A phacoemulsification tip, comprising:
   an aspiration tube presenting a cutting tip at a distal end thereof;
   the aspiration tube having a tube wall presenting an internal face and an external face;
   at least one internally extending pumping structure located proximal of the distal end of the aspiration tube and extending from the internal face into a lumen of the aspiration tube; and
   the at least one pumping structure being configured to create a pumping action when the aspiration tube is vibrated torsionally or elliptically to urge fluid unidirectionally through the lumen to enhance proximal movement of the fluid and lens fragments and to inhibit distal movement of the fluid and the lens fragments through the aspiration tube.

2. The phacoemulsification tip as claimed in claim 1, wherein the at least one pumping structure presents a proximal face and a distal face and the distal face is curved.

3. The phacoemulsification tip as claimed in claim 1, wherein the at least one pumping structure presents a curved distal face and a flat proximal face.

4. The phacoemulsification tip as claimed in claim 1, wherein the at least one pumping structure has an airfoil shape.

5. The phacoemulsification tip as claimed in claim 1, wherein the at least one pumping structure presents a convex distal face and a flat proximal face.

6. The phacoemulsification tip as claimed in claim 1, wherein the phacoemulsification tip is configured to be coupled to a phacoemulsification handpiece including an ultrasonic resonator that vibrates the aspiration tube torsionally or elliptically.

7. The phacoemulsification tip as claimed in claim 1, further comprising at least one outwardly extending external ridge supported by the external face.

8. The phacoemulsification tip as claimed in claim 7, wherein the at least one external ridge is oriented annularly and circumferentially.

9. The phacoemulsification tip as claimed in claim 7, wherein the at least one external ridge is interrupted.

10. The phacoemulsification tip as claimed in claim 7, wherein the at least one external ridge comprises a helical external ridge.

11. The phacoemulsification tip as claimed in claim 7, wherein the at least one external ridge is continuous.

12. A method of phacoemulsification comprising:
    contacting a crystalline lens of an eye with an aspiration tube presenting a cutting tip at a distal end thereof;
    wherein the aspiration tube has a tube wall presenting an internal face and an external face, at least one internally extending pumping structure located proximal of the distal end of the aspiration tube and extending from the internal face into a lumen of the aspiration tube; and
    engaging lens fragments separated from the crystalline lens during phacoemulsification and vibrating the aspiration tube torsionally or elliptically such that the at least one internally extending pumping structure creates or enhances a pumping action that urges fluid unidirectionally through the lumen to enhance proximal movement of the fluid and the lens fragments and to inhibit distal movement of the fluid and the lens fragments through the aspiration tube.

13. The method as claimed in claim 12, further comprising selecting the aspiration tube such that the at least one pumping structure presents a proximal face and a distal face and the distal face is curved.

14. The method as claimed in claim 12, further comprising selecting the aspiration tube such that the at least one pumping structure presents a curved distal face and a flat proximal face.

15. The method as claimed in claim 12, further comprising selecting the aspiration tube such that the at least one pumping structure has an airfoil shape.

16. The method as claimed in claim 12, further comprising selecting the aspiration tube such that the at least one pumping structure presents a convex distal face and a flat proximal face.

17. The method as claimed in claim 12, further comprising selecting the aspiration tube and coupling the aspiration tube to a phacoemulsification handpiece that includes an ultrasonic resonator that vibrates the aspiration tube torsionally or elliptically.

18. The method as claimed in claim 12, further comprising selecting the aspiration tube such that the aspiration tube further comprises at least one outwardly extending external ridge supported by the external face.

19. The method as claimed in claim 18, further comprising selecting the aspiration tube such that the at least one external ridge is continuous.

20. The method as claimed in claim 18, further comprising selecting the aspiration tube such that the at least one external ridge is interrupted.

21. The method as claimed in claim 18, further comprising selecting the aspiration tube such that the at least one external ridge is helical.

* * * * *